United States Patent
Weinberg

(10) Patent No.: US 9,295,408 B2
(45) Date of Patent: Mar. 29, 2016

(54) POINT-OF-CARE NON-INVASIVE ASSAY OF LITHIUM LEVEL

(71) Applicant: WEINBERG MEDICAL PHYSICS LLC, Bethesda, MD (US)

(72) Inventor: Irving N. Weinberg, Bethesda, MD (US)

(73) Assignee: WEINBERG MEDICAL PHYSICS LLC, Bethesda, MD (US)

( * ) Notice: Subject to any disclaimer, the term of this patent is extended or adjusted under 35 U.S.C. 154(b) by 105 days.

(21) Appl. No.: 14/300,887

(22) Filed: Jun. 10, 2014

(65) Prior Publication Data

US 2014/0378824 A1 Dec. 25, 2014

Related U.S. Application Data

(60) Provisional application No. 61/837,823, filed on Jun. 21, 2013.

(51) Int. Cl.
*A61B 5/05* (2006.01)
*A61B 5/055* (2006.01)
*A61B 5/00* (2006.01)
*A61B 5/145* (2006.01)
*G01R 33/465* (2006.01)
*G01R 33/36* (2006.01)

(52) U.S. Cl.
CPC ............... *A61B 5/0555* (2013.01); *A61B 5/055* (2013.01); *A61B 5/14546* (2013.01); *A61B 5/4845* (2013.01); *G01R 33/465* (2013.01); *G01R 33/3635* (2013.01)

(58) Field of Classification Search
CPC .. A61B 5/055; A61B 5/0555; A61B 5/14546; A61B 5/4845; G01R 33/3635; G01R 33/465
See application file for complete search history.

(56) References Cited

U.S. PATENT DOCUMENTS 4,556,068 A * 12/1985 Vartsky ................. A61K 51/02
600/436

* cited by examiner

*Primary Examiner* — Mark Remaly
(74) *Attorney, Agent, or Firm* — Barnes & Thornburg LLP

(57) ABSTRACT

An apparatus and method perform non-invasive lithium measurement of a patient wherein an apparatus comprising a permanent magnet, and at least one radiofrequency coil tuned to the resonant frequency of one or more isotopes of lithium are coupled to a cavity less than 5 cm in diameter in which a subject's body part (other than the subject's brain) can be inserted, wherein, the concentration of lithium in the subject's body is assessed based on one or more measurements of an amount of lithium detected in the body part without the need for withdrawing fluids from the body.

4 Claims, 1 Drawing Sheet

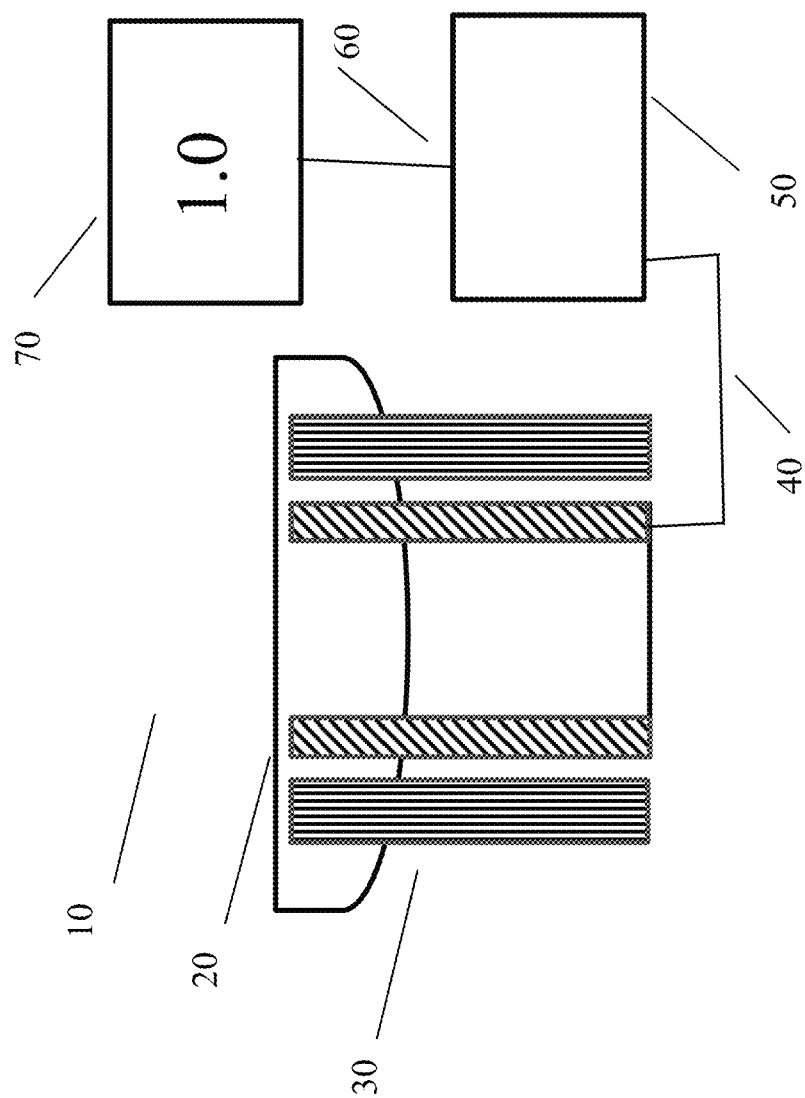

POINT-OF-CARE NON-INVASIVE ASSAY OF LITHIUM LEVEL

CROSS-REFERENCE TO RELATED APPLICATION(S)

This application claims priority to U.S. Provisional Application No. 61/837,823, filed June. 21, 2013, the contents of which are incorporated herein by reference.

FIELD

The disclosed embodiments concern an apparatus and a method for determining lithium levels for point-of-care assays.

BACKGROUND

Patients receiving lithium treatment must undergo regular assays of lithium levels, since the difference between therapeutic and toxic serum concentration levels of this medication is small. Current assays cannot be conducted at the point of care, and require a blood draw. Some individuals who could benefit from lithium treatment do not have regular access to health care facilities with follow-up capabilities, and also may be reluctant to undergo frequent blood draws. In such cases, particularly in emergencies, such individuals could benefit from a rapid assay of lithium levels performed at the point-of-care (for example, at a psychiatrist's office).

Magnetic resonance spectroscopic measurements of lithium levels in the brain have been obtained in vivo using a dual-tuned high-field MRI systems equipped with special radiofrequency (RF) coils, as described by J-H Lee et al, in a scientific article entitled "4T $^7$Li 3D MRSI in the brains of bipolar disorder subjects", published in 2012 in the journal Magnetic Resonance in Medicine (volume 68, issue 2, pages 363-368), incorporated herein by reference.

SUMMARY

Therefore, disclosed embodiments provide an apparatus and a method for performing non-invasive lithium measurement of a patient wherein an apparatus comprising a permanent magnet, and at least one radiofrequency coil tuned to the resonant frequency of one or more isotopes of lithium are coupled to a cavity less than 5 cm in diameter in which a subject's body part (other than the subject's brain) can be inserted, wherein, the concentration of lithium in the subject's body is assessed based on one or more measurements of an amount of lithium detected in the body part without the need for withdrawing fluids from the body.

In accordance with at least one disclosed embodiments, the permanent magnet, at least one radiofrequency coil tuned to the resonant frequency of one or more isotopes of lithium (for example, Lithium-7) and the cavity are used in combination to receive the body part within the cavity, measure an amount of lithium in the body part, and compare the measured amount of lithium with an amount of protons in the body part.

BRIEF DESCRIPTION OF THE DRAWINGS

The invention will now be described in connection with the drawings appended hereto, in which FIG. 1 provides an illustration of equipment provided in accordance with the disclosed embodiments in relationship to a subject's body part. An intact human finger (10) is inserted into a small NMR system. The NMR system is comprised of RF and/or shim coils (20) and permanent magnet (30). RF and/or shim coils (20) are connected via cables (40) to a control and power system (50) which may include RF filter(s) and generator(s), and which in turn is connected via cables or wireless link to computer and/or display system (70). The NMR system may additionally have a calibration sample that may also connected via cables (40) to a control and power system (50) and then in turn to a computer or display system. Computer and/or display system (70) may be remote to the rest of the apparatus, and may be a smartphone.

DETAILED DESCRIPTION

The disclosed embodiments provide a cavity in which an individual may insert a finger. Adjacent to the cavity are components required for conducting magnetic resonance assays for both lithium and protons (for example in water). These components would typically include a permanent magnet, a generator and detector of radiofrequency (RF) electromagnetic waves, and a computer. The RF generator would be coupled to one or more RF coils, which could be alternately tuned to the appropriate frequency (at the magnetic field of the permanent magnet) for lithium atoms (for example, lithium-7) and then to the proton resonance frequency. The gyromagnetic ratio for lithium-7 is about 16 MHz/Tesla, as compared to proton resonance frequency of 42.6 MHz/T.

As illustrated in FIG. 1, an intact human finger (10) is inserted into a small NMR system. The NMR system is comprised of RF and/or shim coils (20) and permanent magnet (30). RF and/or shim coils (20) are connected via cables (40) to a control and power system (50) which may include RF filter(s) and generator(s), and which in turn is connected via cables or wireless link to computer and/or display system (70). Computer and/or display system (70) may be remote to the rest of the apparatus, and may be a smartphone.

Alternatively the disclosed embodiments may include separate coils each tuned to the appropriate frequencies. It is contemplated that shimming electromagnets and/or permanent magnets may be present in the vicinity of the cavity. It is also possible that calibration samples that could be comprised of fluorine-19 with an associated RF receive coil may also be present within the cavity. Unlike the previously-described dual-tuned high-field MRI, the current invention uses permanent magnets at low field strength and does not examine the head. Unlike serum measurement of lithium, the current invention does not require removal of fluids from the body.

Operation of a method performed in accordance with the disclosed embodiments may include the collection of data correlated to the concentration of lithium in the cavity and of protons in the cavity. In one embodiment, the signal corresponding to the concentration of lithium would be compared to the signal corresponding to the concentration of water in the cavity.

The invention claimed is:

1. An apparatus comprising:
a permanent magnet;
at least one radiofrequency coil tuned to the resonant frequency of at least one isotope of lithium; and
a cavity less than 3 cm in diameter in which a body part can be inserted.

2. The apparatus of claim 1, wherein an amount of lithium in the body part is compared with an amount of protons in the body part.

3. A method of assessing the concentration of lithium in a body by measuring an amount of lithium detected in a body part other than the brain without the need for withdrawing fluids from the body, the method comprising:

providing a permanent magnet;

tuning at least one radiofrequency coil to the resonant frequency of at least one isotope of lithium;

receiving a body part within a cavity less than 5 cm in diameter; and measuring an amount of lithium in the body part.

4. The method of claim 3, further comprising comparing the measured amount of lithium with an amount of protons in the body part.

* * * * *